US010001446B2

(12) United States Patent
Szudajski et al.

(10) Patent No.: US 10,001,446 B2
(45) Date of Patent: Jun. 19, 2018

(54) CORE SAMPLE ANALYSIS

(71) Applicant: GE Energy Oilfield Technology, Inc., Houston, TX (US)

(72) Inventors: Thomas Szudajski, Houston, TX (US); John Boot, Atlanta, GA (US)

(73) Assignee: GE Energy Oilfield Technology, Inc., Houston, TX (US)

( * ) Notice: Subject to any disclaimer, the term of this patent is extended or adjusted under 35 U.S.C. 154(b) by 0 days. days.

(21) Appl. No.: 14/536,325

(22) Filed: Nov. 7, 2014

(65) Prior Publication Data

US 2016/0131602 A1 May 12, 2016

(51) Int. Cl.
*G01N 23/04* (2018.01)
*G01N 33/24* (2006.01)

(52) U.S. Cl.
CPC ........... *G01N 23/046* (2013.01); *G01N 33/24* (2013.01); *G01N 2223/301* (2013.01); *G01N 2223/3305* (2013.01); *G01N 2223/616* (2013.01)

(58) Field of Classification Search
CPC ........... G01N 23/046; G01N 2223/419; G01N 2223/616
USPC ............................. 250/255, 269.1; 280/402
See application file for complete search history.

(56) References Cited

U.S. PATENT DOCUMENTS

| 3,704,898 | A | 12/1972 | Schmidt |
| 3,746,369 | A | 7/1973 | Neff |
| 4,244,417 | A | 1/1981 | Taylor |
| 4,571,491 | A * | 2/1986 | Vinegar ............... G01N 23/083 250/252.1 |
| 4,616,134 | A * | 10/1986 | Pruett ................ G01N 21/5911 250/255 |
| 4,909,557 | A | 3/1990 | De Weck et al. |
| 4,977,586 | A | 12/1990 | Curry |
| 5,025,150 | A * | 6/1991 | Oldham .................. G01V 5/02 250/253 |
| 5,153,899 | A | 10/1992 | Curry |
| 5,318,123 | A | 6/1994 | Venditto et al. |
| 5,360,066 | A | 11/1994 | Venditto et al. |
| 5,386,875 | A | 2/1995 | Venditto et al. |
| 5,409,251 | A | 4/1995 | Thorndyke |
| 5,509,687 | A | 4/1996 | Thorndyke |
| 5,712,893 | A | 1/1998 | Dykster et al. |
| 5,947,213 | A * | 9/1999 | Angle ..................... E21B 4/18 166/250.01 |
| 6,430,547 | B1 | 8/2002 | Busche |

(Continued)

FOREIGN PATENT DOCUMENTS

GB 2135049 8/1984

*Primary Examiner* — David Porta
*Assistant Examiner* — Blake Riddick
(74) *Attorney, Agent, or Firm* — Hogan Lovells US LLP (57) ABSTRACT

A method and system for analyzing a core sample from a wellbore, where the analysis takes place in the field and proximate the wellbore. The system includes trailers adjacent one another. One of the trailers can include a unit for scanning the core sample and obtaining information within the sample. Other trailers can include units that further analyze the core, such as by grinding, laser spectroscopy, and Raman spectroscopy. The core sample scanning involves a computerized tomography (CT) scan, where a length of core is analyzed in the scanning unit. The unit includes a manipulator system for moving the core sample through a rotating scan source in the scanning unit.

17 Claims, 5 Drawing Sheets

(56) References Cited

U.S. PATENT DOCUMENTS

| | | |
|---|---|---|
| 6,481,887 B1 | 11/2002 | Mirabella |
| 6,816,787 B2 | 11/2004 | Ramamoorthy |
| 6,940,941 B2 | 9/2005 | Gregerson et al. |
| 7,082,185 B2 | 7/2006 | Freifeld et al. |
| 7,113,569 B2 | 9/2006 | Okumura et al. |
| 7,175,347 B2 | 2/2007 | Tybinkowski et al. |
| 7,564,944 B2 | 7/2009 | Kato |
| 7,714,304 B2 | 5/2010 | Poglitsch |
| 7,853,045 B2 | 12/2010 | Touati |
| 7,866,386 B2 | 1/2011 | Beer et al. |
| 8,068,579 B1 | 11/2011 | Yun et al. |
| 8,081,796 B2 | 12/2011 | Derzhi et al. |
| 8,081,802 B2 | 12/2011 | Dvorkin et al. |
| 8,085,974 B2 | 12/2011 | Dvorkin et al. |
| 8,155,377 B2 | 4/2012 | Dvorkin et al. |
| 8,170,799 B2 | 5/2012 | Dvorkin et al. |
| 8,234,912 B2 | 8/2012 | Suarez-Rivera et al. |
| 8,327,932 B2 | 12/2012 | Karanikas et al. |
| 8,331,626 B2 | 12/2012 | Wojcik et al. |
| 8,542,793 B1 | 9/2013 | Jin |
| 8,562,078 B2 | 10/2013 | Bums et al. |
| 8,590,382 B2 | 11/2013 | Zaleski, Jr. et al. |
| 8,636,323 B2 | 1/2014 | Prince-Wright et al. |
| 8,657,000 B2 | 2/2014 | Willingham et al. |
| 8,725,477 B2 | 5/2014 | Zhang et al. |
| 9,063,247 B2 | 6/2015 | Li et al. |
| 9,103,176 B2 | 8/2015 | Delmar et al. |
| 9,196,058 B2 | 11/2015 | Mezghani |
| 9,507,047 B1 | 11/2016 | Dvorkin et al. |
| 9,573,434 B2 | 2/2017 | Boot et al. |
| 2002/0018542 A1 | 2/2002 | Fenkart et al. |
| 2003/0107735 A1* | 6/2003 | Bland .................. G01N 15/0227 356/338 |
| 2004/0218716 A1 | 11/2004 | Freifeld et al. |
| 2005/0127620 A1 | 6/2005 | Amundson |
| 2008/0217559 A1* | 9/2008 | Poglitsch ............. G01N 23/046 250/491.1 |
| 2009/0078467 A1* | 3/2009 | Castillo .................. E21B 25/10 175/249 |
| 2010/0250139 A1* | 9/2010 | Hobbs ..................... E21B 47/12 702/6 |
| 2011/0150177 A1* | 6/2011 | Nielsen Groot ....... A61B 6/107 378/20 |
| 2012/0136196 A1* | 5/2012 | Foxall ................... A61B 5/055 600/21 |
| 2012/0148398 A1 | 6/2012 | Campbell et al. |
| 2013/0083888 A1 | 4/2013 | Jin |
| 2013/0182819 A1 | 7/2013 | Dvorkin et al. |
| 2013/0301794 A1 | 11/2013 | Grader et al. |
| 2014/0119501 A1 | 5/2014 | O'Hare et al. |
| 2014/0367086 A1* | 12/2014 | Arian ..................... E21B 49/06 166/244.1 |
| 2015/0044004 A1 | 2/2015 | Pham et al. |

\* cited by examiner

CORE SAMPLE ANALYSIS

BACKGROUND OF THE INVENTION

1. Field of Invention

The present disclosure relates in general to a method and system for analyzing a core sample from a wellbore. More specifically, the present disclosure relates to a method and system for evaluating a core sample from a wellbore with computerized tomography.

2. Description of Prior Art

Various techniques are currently in use for identifying the presence of hydrocarbons in subterranean formations. Some techniques employ devices that emit a signal from a seismic source, and receive reflections of the signal on surface. Others involve disposing logging devices downhole in a wellbore intersecting the subterranean formation, and interrogating the formation from within the wellbore. Example downhole exploration devices include seismic tools that can transmit and receive seismic signals, or ones that simply receive a seismic signal generated at surface. Other devices collect and sample fluid from within the formation, or from within the wellbore. Nuclear tools are also employed that direct radiation into the formation, and receive radiation that scatters from the formation. Analyzing the scattered radiation can provide information about fluids residing in the formation adjacent the wellbore, the type of fluid, and information about other materials next to the wellbore, such as gravel pack.

Logging downhole also is sometimes done while the wellbore itself is being drilled. The logging devices are usually either integral with a drill bit used during drilling, or on a drill string that rotates the drill bit. The logging devices typically are either nuclear, seismic, can in some instances optical devices. In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample.

SUMMARY OF THE INVENTION

Disclosed herein is an example of a system for analyzing a core sample and which includes a first mobile enclosure having a scan system, a second mobile enclosure adjacent the first mobile enclosure, a loading assembly having an end coupled to the scan system and that projects into the second mobile enclosure, and a loading cover on a portion of the loading assembly that projects into the second mobile enclosure, and that selectively receives the core sample. The system can further include a hatch assembly mounted between the first and second mobile enclosures and circumscribing the loading assembly. Stations are optionally included in the second mobile enclosure where sections of the core sample are removed for further analysis. The system can further include a third mobile enclosure proximate the first and second mobile enclosures, and a laser based material analyzer in the third mobile enclosure. In an example, a manipulator is included with the system and that is in the first mobile enclosure, manipulator includes a core carrier on which the core sample is selectively disposed, and that selectively and in a synchronized fashion reciprocates the core sample within the scan system. In this example, the manipulator further includes a manipulator base in the first mobile enclosure, and a manipulator arm that is selectively and telescopingly urged along the manipulator base. Further in this example the scan system has a gantry system with a scan source that emits scan energy and orbits about an axis, a scan receiver that also orbits about the axis and that receives energy deflected from the core sample when the core sample is inserted within the orbiting scan source and scan receiver. In an example, the core carrier is selectively moveable in an X, Y, and a Z axis. Interlock connectors may be included on the loading cover that are in communication with a controller, so that when the loading cover is in an open position, power to the scan system is blocked. The scan system can be a computerized topography scanner. Optionally, the first and second mobile enclosures each are a trailer portion of a uniquely equipped tractor trailer rig.

Also disclosed herein is a method of analyzing a core sample which includes providing a first mobile enclosure having a scan system with a loading assembly, disposing the first mobile enclosure proximate a wellbore, disposing a second mobile enclosure adjacent the first mobile enclosure and so that a portion of the loading assembly projects into the second mobile enclosure, disposing the core sample into the second mobile enclosure and inserting the core sample into the loading assembly, and scanning the core sample with the scan system. The core sample can be removed from the scan system so that sections of the core sample can be removed for further analysis to form sample portions. The sections removed from the core sample can be analyzed in a laser based material analyzer. A manipulator can be operated that axially moves the core sample in the scan system. The method can also include orbiting a source of scan energy around the core sample while the core sample is in the scan system, and obtaining scan energy that penetrates and is deflected from the core sample. The method can further involve conducting an initial scan of the core sample, and repositioning the core sample in the scan system based on an analysis of the initial scan. In this example, the step of repositioning the core sample includes adjusting a position of the core sample, such as its elevation, lateral position, or combinations thereof. The method can include identifying an area of interest based on the initial scan for which additional analysis is performed. The step of disposing the first and second mobile enclosures can be to pull the first and second mobile enclosures with a tractor.

BRIEF DESCRIPTION OF DRAWINGS

Some of the features and benefits of the present invention having been stated, others will become apparent as the description proceeds when taken in conjunction with the accompanying drawings, in which.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes, but is not necessarily limited to, +/−5% of the cited magnitude. In an embodiment, usage of the term "substantially" includes, but is not necessarily limited to, +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figure 1:
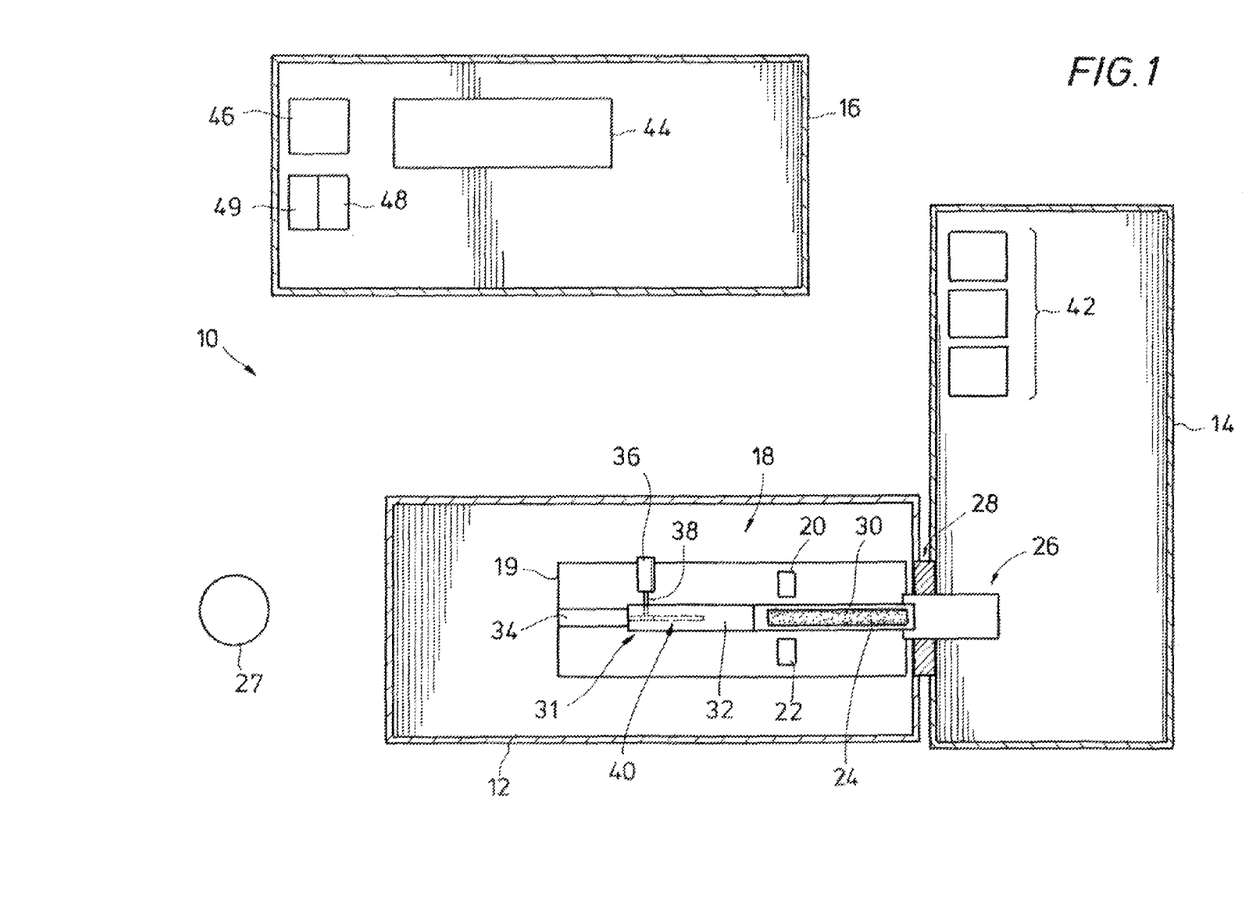
FIG. 1 is a plan partial sectional view of an example of a system for analyzing a core sample.

Shown in a plan partial sectional view in FIG. 1 is one example of a core analysis system 10, which includes first, second and third mobile enclosures. In the example of FIG. 1, the first mobile enclosure is a scan trailer 12, the second mobile enclosure is a handling trailer 14, and the third mobile enclosure is an analysis trailer 16. In one example, each of the enclosures may be part of a tractor trailer and which are movable by a tractor trailer. Schematically illustrated in the scan trailer 12 is a scan system 18, and substantially all of which is housed within a cabinet 19. In the illustrated example, cabinet 19 is specially designed to shield any radiation within, generated, inherent, or otherwise, from making its way to outside of the cabinet 19. Thus, cabinet 19 is in compliance with 21 C.F.R. 1020.40. Further shown in cabinet 19 is a scan source 20, which in one embodiment includes a device for emitting radiation, such as but not limited to an X-ray, microwave, millimeter wave, etc. A scan receiver 22 is also shown provided within cabinet 19 and combined with scan source 20, in one example, forms a Computed Tomography (CT) scanner.

An elongate and cylindrical core sample 24 is shown axially inserted within scan system 18. Core sample 24 is disposed into scan system 18 through a loading assembly 26, which is shown coupled to one end of the scan system 18 and projecting through an opening in a side wall of handling trailer 14. In an example, core sample 24 is taken from a subterranean formation below system 10, and is retrieved via a wellbore 27 shown adjacent system 10. Thus the wellbore 27 intersects the subterranean formation. Embodiments exist where the system 10 is "onsite" in the field and where the distance between the wellbore 27 to system 10 can range from less than one hundred yards up to five miles, and any distance between. Accordingly, real time analysis while drilling the wellbore 27 can take place within the system 10. Feedback from the analysis can be used by the drilling operator to make adjustments or changes to the drilling operation.

A hatch assembly 28 is schematically illustrated which provides the coupling interface between trailers 12, 14 and includes sealing around the loading assembly 26. While in scan system 18, core sample 24 rests on a core carrier 30. In an example, core carrier 30 is fabricated from a material transparent to X-Rays, and can support the load of the core sample 24 with minimum deflection to maintain the resolution of a stationary scanner. Core carrier 30 is part of a manipulator system 31, which further includes a manipulator arm 32 that telescopingly moves along a manipulator base 34. As shown, an end of manipulator arm 32 distal from manipulator base 34 couples onto an end of core carrier 30, so that core carrier is basically cantilevered on an end of the manipulator arm 32. Manipulator arm 32 is shown in an extended position over manipulator base 34. Manipulator arm 32 axially moves with respect to manipulator base 34 via a motor 36 shown having a shaft 38 that couples to manipulator arm 32. In one example, motor 36 is a linear direct current motor. A gear (not shown) on an end of shaft 38 distal from motor 36 engages a gear rack 40 that is provided on manipulator arm 32. Accordingly, selectively operating motor 36 urges manipulator arm 32, core carrier 30 and core sample 24 in an axial direction with respect to scan source 20. Moving manipulator arm 32 into a refracted position onto manipulator base 34 positions the entire length of core sample 24 in scan system 18, so that all of core sample 24 may be analyzed by the scan system 18. In one example, the scan source 20 and scan receiver 22 orbit around the core sample 24 and so that when in combination of axial movement of core sample 24 within system 18, a helical scan is taken of core sample 24. Further optionally, motor 36, or additional motors not shown, may manipulate and selectively move manipulator arm vertically and/or laterally to thereby better position core sample 24 into a designated orientation and/or spatial position during the scanning process.

Further shown in FIG. 1 are a series of work surfaces 42 provided within handling trailer 14. In one example of operation, before or after core sample 24 is scanned, it may be broken into sections for further analysis and analyzed on surfaces 42. Examples of the surfaces 42 include a crusher, sample divider, and mortar grinder. Additional analysis may take place within analysis trailer 16. Schematically illustrated within analysis trailer 16 are a variety of analysis equipment such as, but not limited to, scanners and spectrometers. One such analysis equipment is a nanotom 44, which can include a scanning system for scanning the internals of core sample 24, or parts of the core sample. Further analysis equipment in the analysis trailer 16 may be a laser induced spectroscope 46, a Raman spectroscope 48, and near infrared spectroscope 49. It will be understood that alternate embodiments may include more trailers or fewer trailers. For example, an appropriately sized scan system 18 may allow loading assembly 26 to be in scan trailer 12 without projecting through an opening in the trailer and without a hatch assembly 28. A further embodiment may provide work surfaces 42 in the same trailer as the analysis equipment, or the analysis equipment may be contained in handling trailer 14. In yet a further embodiment, scan system 18, loading assembly 26, work surfaces 42 and analysis equipment (e.g., nanotom 44, spectroscopes 46, 48, 49, or others) are all contained in one trailer.

Figure 2:
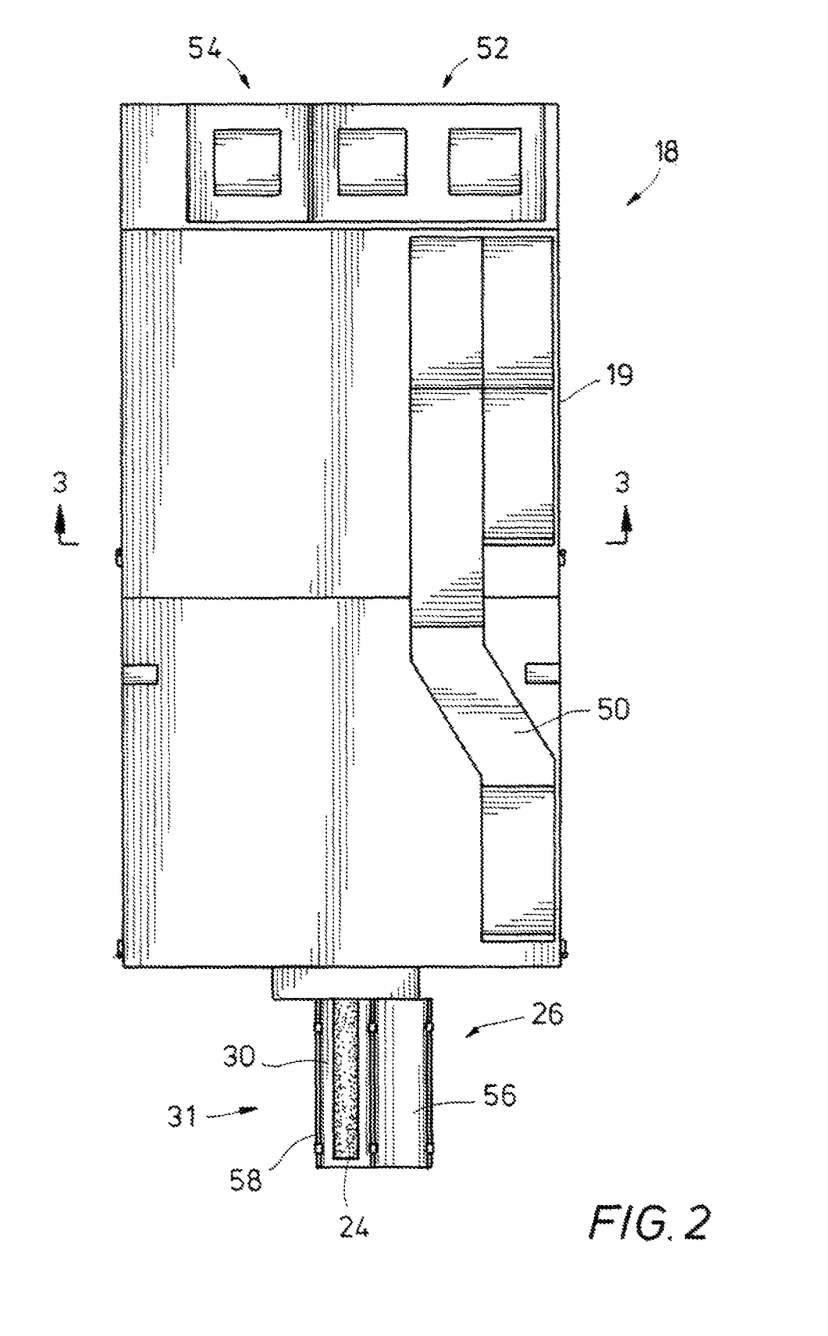
FIG. 2 is an overhead view of an example of a cabinet for shielding radiation and conditioning a scanning unit for a core sample.

Referring now to FIG. 2, shown in an overhead view is an example of the scan system 18 and an upper surface of cabinet 19. Further illustrated in this example is a conditioning vent 50 on an upper end of the cabinet 19, where conditioning vent 50 provides a path for airflow and that is used in conditioning the inside of the cabinet 19, while blocking the leakage of any radiation from cabinet 19. An advantage of the conditioning vent 50 is that conditioned air at proper temperature and humidity may be injected into the inside of cabinet 19 so that the sensitive devices housed within the cabinet 19 may be maintained in proper operating conditions to ensure normal operating functionality. In an example, operational conditions require maintaining a substantially constant temperature within the cabinet 19. In one embodiment, the temperature variation in the cabinet 19 is kept of within 2 degrees C. of a designated temperature. An advantage of the device described herein is that the temperature in the cabinet 19 can be maintained within the designated range in spite of substantial air replacement. Air replacement in the cabinet 19, due to the loading mechanism operation, maintains temperature uniformity across the scanner frame and rotary element. In one example, the volumetric rate of air replacement is at least about 4 $m^3$/min. A power distribution panel 52 is shown provided at an aft end of cabinet 19, and which includes buses (not shown) and other devices for distributing power through cabinet 19 into scan system 18. A control panel 54 is shown adjacent power distribution panel 52 and includes hardware and software for managing control of the operation of the systems house within cabinet 19. Projecting outward past the forward end of cabinet 19 is the loading assembly 26 in an open configuration. In the illustrated example, the loading assembly 26 includes a loading cover 56 and loading basin 58, where the loading cover 56 is shown swung open from a loading basin 58. As shown the core sample 24 has been inserted into open loading assembly 26 and onto the core carrier 30. As will be described in more detail below, safety features are included with the system that prevent operation of the manipulator system 31 when the loading assembly 26 is in the open position of FIG. 2.

Figure 3:
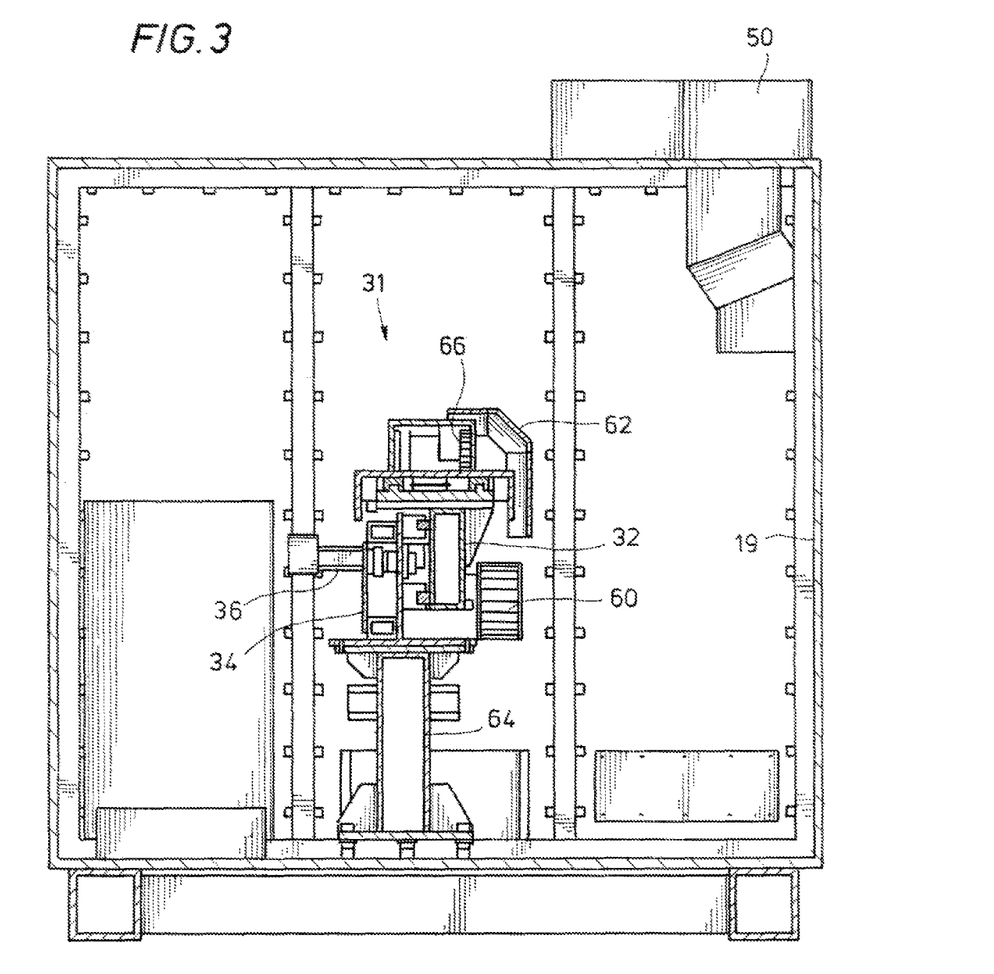
FIG. 3 is an axial sectional view of the cabinet of FIG. 2 and taken along lines 3-3.

FIG. 3 shows an example of the cabinet 19 in a sectional view and taken along lines 3-3 of FIG. 2. This view which is taken along the axial portion of manipulator system 31 shows one example of a wiring track 60; which has cross members for organizing the control and power wires needed for use in the scan system 18 and as the manipulator arm 32 axially moves with respect to manipulator base 34. Wiring track 60 maintains the wires in a designated location and position with use of wiring track 60 during operation of the manipulator system 31. Further in the example of FIG. 3 is a shroud 62 shown mounted on an upper end of manipulator system 31 and which covers a portion of the upper end and shields components within the manipulator system 31. Manipulator base 34 (and thus manipulator arm 32) is supported on a vertical mounting pedestal 64, which has a generally rectangular cross section along its axis, and has a lower end mounted on the floor of cabinet 19. Shown housed within shroud 62 is a wiring bus 66 which extends axially along the manipulator assembly.

Figure 4:
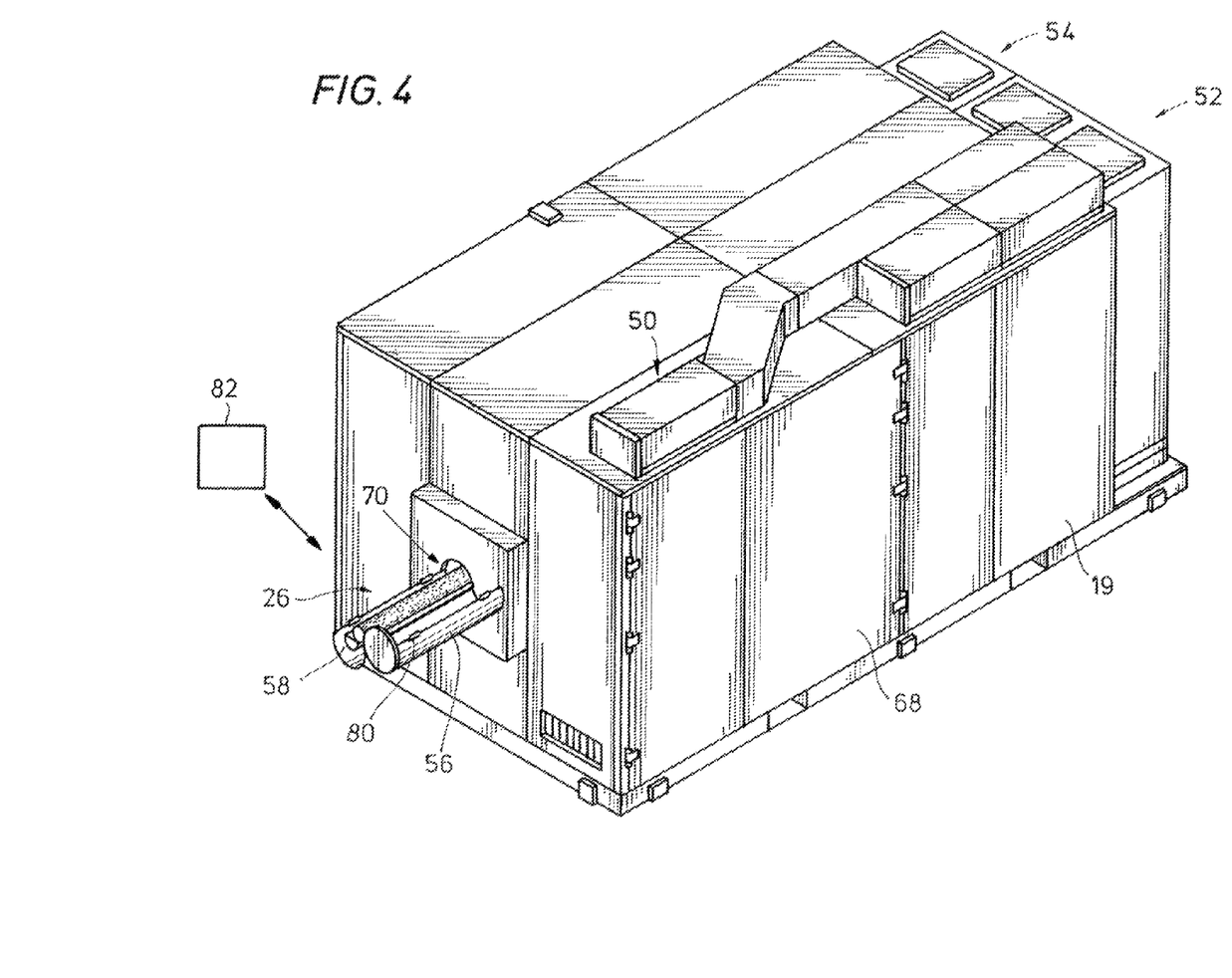
FIG. 4 is a perspective view of the cabinet of FIG. 2.

FIG. 4 provides in perspective view of one example of the cabinet 19 and having hinged panel 68 along its outer surface. As indicated above, the structure of cabinet 19 is in compliance with 21 C.F.R. 1020.40. Thus proper protective shielding and interlocking is provided in the panel 68 and along the hinged interface. An additional safety feature is a door assembly 70 which includes a barrier (not shown) that slides axially across the opening shown at the base of the loading assembly 26 and in a forward wall of cabinet 19. The barrier thus provides a radiation shield from the inside to the outside of cabinet 19 while still allowing core sample loading in compliance with 21 C.F.R. § 1020.40.

Figure 5:
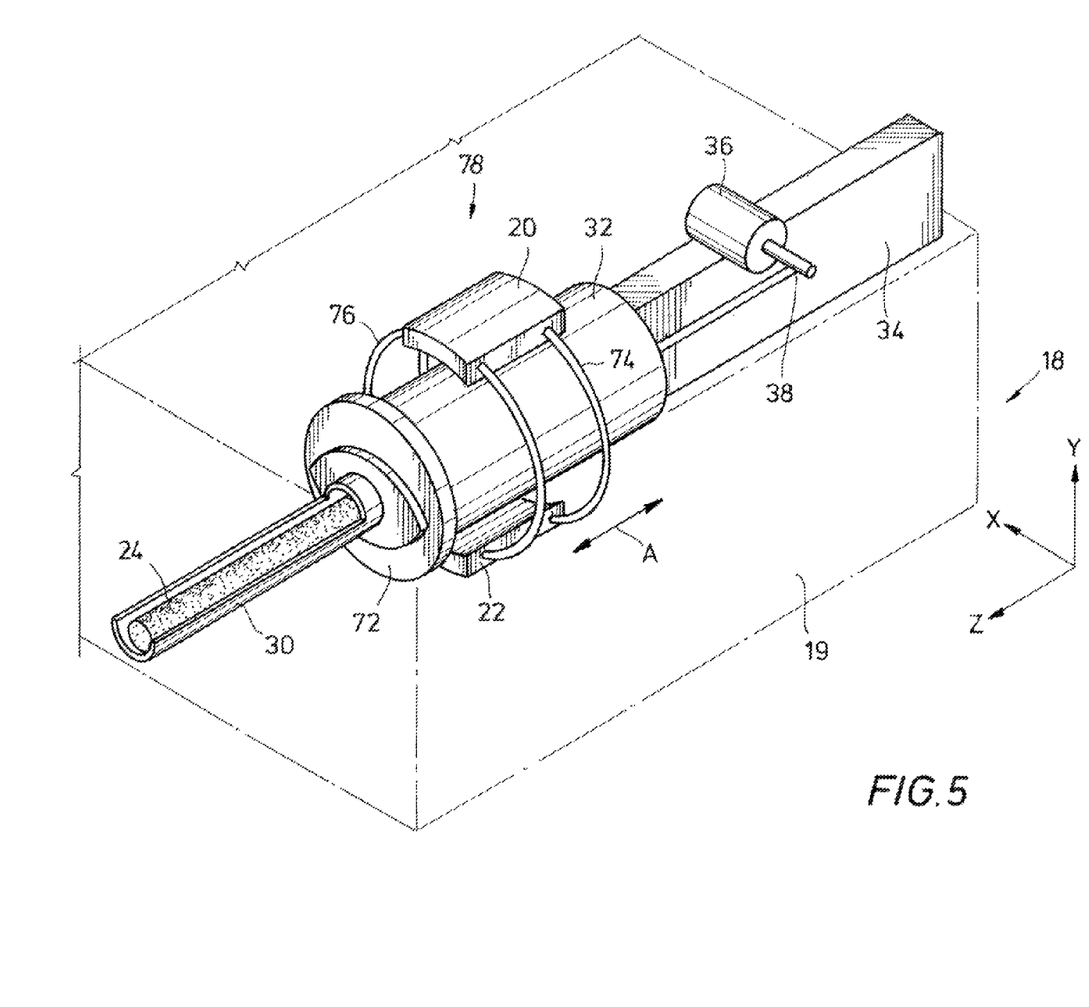
FIG. 5 is a perspective view of the cabinet of FIG. 2 in partial phantom view and an example scanning unit in the cabinet.

An example of the manipulator assembly within cabinet 19 is illustrated in perspective view in FIG. 5, and where cabinet 19 is shown in a partial phantom view. In this embodiment, a rearward end of manipulator base 34 is supported on a rearward end of cabinet 19; manipulator base 34 extends axially away from the rearward wall of cabinet 19 with the manipulator arm 32 axially sliding on manipulator base 34. Motor 36 is shown oriented generally perpendicular to an axis of manipulator arm 32 and manipulator base 34, and couples to manipulator arm 32 by shaft 38. Further illustrated is how the core carrier 30 couples to a mounting plate 72; where mounting plate 72 is a generally circular and planar member that mounts on a forward end of manipulator arm 32. In one embodiment, this member along with an extended tunnel provides the seal that inhibits excessive air flow during the loading process.

Axial movement, as shown by the double headed arrow A, of core sample 24 is accomplished via motor 36. X, Y, and Z axes are illustrated to define an example coordinate system for the purposes of reference herein. While not limited to this coordinate system, the axes depict axial movement of any object, such as the core sample 24, to be along the Z axis, vertical movement to be along the Y axis, and lateral movement to be along the X axis. As indicated above, operation of motor 36 can move core sample 24 along all of these axes. Further shown in FIG. 5 are curved supports 74, 76 that circumscribe manipulator arm 32 and provide a mounting surface for scan source 20 and scan receiver 22. The combination of the support 74, 76 define a gantry 78 that when rotated puts the scan source 20 and scan receiver 22 at an orbiting rotation around the core sample 24 and provides the scanning capabilities of the scan system 18. As indicated above, the air replacement capabilities provided with cabinet 19 maintains a substantially constant temperature across the gantry 78.

Referring back to FIG. 4, an interlock connector 80 is shown provided on the loading cover 56 and loading basin 58. The interlock connectors 80 thus may recognize when the cover 56 is in the open position of FIG. 4 and in combination with controller 82 may prevent operation of the manipulator assembly. However, the control system associated with the scan system 18 that allows for motion of the manipulator assembly when the cover 56 is in the closed position and interlock connectors are adjacent one another.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. For example, in an embodiment, mounting and shock absorption hardware is provided for securing the components in the core analysis system 10 to maintain their integrity and alignment during transportation in the trailers. The gantry can include reinforced mounting for rotating elements and added adhesive for board mounted components, e.g. integrated circuitry, resistors, capacitors, and the like. A transport locking mechanism can be used to prevent sliding door movement when power is removed, and a locking mechanism can be used on all threaded fasteners. All circuit boards can be mechanically secured to reduce vibration and remove gravity loading on connectors. Relays can be secured to mounting sockets, and expansion loops can be added in all cables and hoses and secured to cabinet walls. High voltage cables can be cushioned, and service door fastening can be added to prevent load on interlock closure. Cooling fan mounting can be reinforced and cooler unit can be secured for shipment. Also, transformer can be set near high voltage generator by mounting to the floor of the cabinet. An advantage of this is a scanned image of the core sample 24 can be produced at a resolution of up to 200 microns. These and other similar modifications will readily suggest themselves to those skilled in the art, and are intended to be encompassed within the spirit of the present invention disclosed herein and the scope of the appended claims.

What is claimed is:

1. A system for assessing a core sample comprising:
   a mobile enclosure;
   an analysis system within the mobile enclosure;
   a loading assembly coupled to the analysis system, projecting through a wall of the mobile enclosure, and that selectively receives the core sample, the loading assembly having a loading basin and a loading cover, the loading cover selectively movable relative to the loading basin between an open position and a closed position, the core sample isolated within the loading basin when the loading cover is in the closed position; and
   a manipulator in the mobile enclosure having a core carrier on which the core sample is selectively disposed, and that selectively reciprocates the core sample within the analysis system, the manipulator disabled when the loading cover is in the open position.

2. The system of claim 1, wherein the mobile enclosure is sealed, and isolates a scan system within the mobile enclosure from an ambient environment outside the mobile enclosure.

3. The system of claim 2, further comprising a hatch assembly mounted to the mobile enclosure and circumscribing the loading assembly to maintain the sealed nature of the mobile enclosure.

4. The system of claim 1, wherein the analysis system comprises one of a scanning system and a spectroscopy system.

5. The system of claim 1, further comprising stations where sections of the core sample are removed and are further analyzed in a second analysis system.

6. The system of claim 1, wherein the manipulator further comprises a manipulator base in the mobile enclosure, and a manipulator arm that is selectively and telescopingly urged along the manipulator base.

7. The system of claim 1, wherein the analysis system comprises a gantry system comprising a scan source that emits scan energy and orbits about an axis, a scan receiver that also orbits about the axis and that receives energy deflected from the core sample when the core sample is inserted between the orbiting scan source and scan receiver.

8. The system of claim 1, wherein the core carrier is selectively moveable in an X, Y, and a Z axis.

9. The system of claim 1, further comprising interlock connectors on the loading cover that are in communication with a controller, so that when the loading cover is in an open position, power to the analysis system is blocked.

10. The system of claim 1, wherein the analysis system comprises a computed tomography scanner.

11. The system of claim 1, wherein the mobile enclosure comprises a trailer portion of a tractor trailer rig.

12. A method of assessing a core sample comprising:
    providing a sealed mobile enclosure having an analysis system with a loading assembly, the sealed mobile enclosure isolating a scan system within the sealed mobile enclosure from an ambient environment outside the sealed mobile enclosure, and the loading assembly projecting through a wall of the sealed mobile enclosure, the loading assembly having a loading basin and a loading cover, the loading cover selectively movable relative to the loading basin between an open position and a closed position, the core sample isolated within the loading basin when the loading cover is in the closed position;
    disposing the mobile enclosure proximate a wellbore;
    analyzing the core sample with the analysis system; and
    operating a manipulator that axially moves the core sample in the scan system, the manipulator disabled when the loading cover is in the open position.

13. The method of claim 12, further comprising removing the core sample from the scan system and removing sections of the core sample to form sample portions which are further analyzed in a second analysis system.

14. The method of claim 13, wherein the second analysis system is a spectrometer.

15. The method of claim 12, further comprising orbiting a source of scan energy around the core sample while the core sample is in the scan system, and obtaining scan energy that is deflected from the core sample.

16. The method of claim 12, further comprising conducting an initial scan of the core sample, and repositioning the core sample in the scan system based on an analysis of the initial scan.

17. The method of claim 12, wherein the step of disposing the mobile enclosure comprises pulling the mobile enclosure with a tractor.

\* \* \* \* \*